United States Patent [19]

Hirsch-Kauffmann

[11] Patent Number: 5,134,165

[45] Date of Patent: Jul. 28, 1992

[54] METHOD OF TREATMENT FOR LOSS OF VISION DUE TO OPHTHALMIC SURGERY

[76] Inventor: Dan J. Hirsch-Kauffmann, 1-2 Grammatan Ct., Bronxville, N.Y. 10708

[21] Appl. No.: 364,469

[22] Filed: Jun. 9, 1989

[51] Int. Cl.$^5$ ............................................. A61K 31/19
[52] U.S. Cl. ................................... 514/568; 514/912
[58] Field of Search ..................... 514/568, 512, 912

[56] References Cited

U.S. PATENT DOCUMENTS

| | | | |
|---|---|---|---|
| 3,681,445 | 8/1972 | Ruyle et al. | 260/520 |
| 3,714,226 | 1/1973 | Ruyle et al. | 260/473 S |
| 4,044,049 | 8/1977 | Ruyle et al. | 260/479 R |
| 4,542,158 | 9/1985 | Dorn | 514/512 |
| 4,720,503 | 1/1988 | Witzel et al. | 514/443 |
| 4,749,721 | 6/1988 | Sunshine et al. | 514/532 |

OTHER PUBLICATIONS

Flach et al, "The Effect of Ketorolac Tromethamine Solution 0.5% in Reducing Postoperative Inflammation after Cataract Extraction and Intraocular Lens Implantation", Ophthamology, 95:9:1279-1284, Sep. 1988.

Cox et al, "Treatment of Chronic Macular Edema With Acetazolamide", Arch Ophthamology, 106:1190-1195, Sep. 1988.

Flach et al, "Effectiveness of Ketorolac Tromethamine 0.5% Ophthalmic Solution for Chronic Aphakic and Pseudophakic Cystoid Macular Edema", Am. Journ. Ophthalmology, 103:479-486, Apr. 1987.

Jampol, "Aphakic Cystoid Macular Edema", Arch Ophthalmology, 103:1134-1135, Aug. 1985.

Jampol, "Pharmacologic Therapy of Aphakic and Pseudophakic Cystoid Macular Edema", Ophthalmology, 92:6:807-810, Jun. 1985.

Jampol, "Prophylaxis and Therapy of Aphakic Cystoid Macular Edema", Survey of Ophthalmology, 28:Supp:5-35-539, May 1984.

Miyake, "Indomethacin in the Treatment of Postoperative Cystoid Macular Edema", Survey of Ophthalmology, 28:Supp:554-568, May 1984.

Fung, "The National, Prospective, Randomized Vitrectomy Study for Chronic Aphakic Cystoid Macular Edema", Progress Report and Comparison Between the Control and Nonrandomized Groups, Survey of Ophthalmology, 28:Supp:569-576, May 1984.

Sanders et al, "Aqueous Penetration of Oral and Topical Indomethacin in Humans", Arch Ophthalmology, 101:1614-1616, Oct. 1983.

Miyake et al, "Incidence of Cystoid Macular Edema After Retinal Detachment Surgery and the Use of Topical Indomethacin", Am. Journal of Ophthalmology, 95:451-456, 1983.

Yannuzzi et al, "Incidence of Aphakic Cystoid Macular Edema with the Use of Topical Indomethacin", Ophthalmology, 88:9:947-953, Sep. 1981.

Severin, "Late Cystoid Macular Edema in Pseudophakia", Am. Journ. of Ophthalmology, 90:223-225, 1980.

Klein et al, "The Effect of Indomethacin Pretreatment on Aphakic Cystoid Macular Edema", Am. Journ. of Ophthalmology, 87:487-489, 1979.

Jacobson et al, "Natural History of Cystoid Macular Edema After Cataract Extraction", Am. Journ. of Ophthalmology, 77:4:445-447, Apr. 1974.

Jampol, "Pharmacologic Therapy of Aphakic Cystoid Macular Edema", Ophthalmology, 89:8:891-897, Aug. 1982.

Sanders et al, "Breakdown and Reestablishment of Blood-Aqueous Barrier With Implant Surgery", Arch of Ophthalmology, 100:588-590, Apr. 1982.

Kraff et al, "Prophylaxis of Pseudophakic Cystoid Macular Edema with Topical Indomethacin", Ophthalmology, 89:8:885-890, Aug. 1982.

Ronen et al., "Treatment of Ocular Inflammation With Diclofenac Sodium: Double-Blind Trial Following Cataract Surgery", Ann. Ophthalmology, 17:577-581, (1985).

Katz, "Indomethacin", Ophthamology, 88:5:455-458, May 1981.

Primary Examiner—Frederick Waddell
Assistant Examiner—Zohreh A. Fay
Attorney, Agent, or Firm—Hedman, Gibson & Costigan

[57] ABSTRACT

A method of preventing an impairment of vision induced by ophthalmic surgery or improving the vision impaired by ophthalmic surgery of a warm-blooded animal is provided which comprises administering either a prophylactically effective or a therapeutically effective amount of diflunisal either systemically or topically to the animal. An optional maintenance effective amount of diflunisal may be subsequently administered. A topical dosage unit form of diflunisal is also provided.

11 Claims, No Drawings

METHOD OF TREATMENT FOR LOSS OF VISION DUE TO OPHTHALMIC SURGERY

FIELD OF THE INVENTION

The invention relates to a method for the prevention or the reduction of an impairment of vision of the eye of warm-blooded animals when the vision is subject to impairment or has been impaired by ophthalmic surgery. Diflunisal is administered, either systemically or topically to the outer surface of the eye, either in a prophylactically effective amount or in a therapeutically effective amount.

The administration of diflunisal can prevent the development of cystoid macular edema of the eye induced by ophthalmic surgery in warm-blooded animals, particularly in those who will undergo or have undergone cataract removal surgery and/or subsequent artificial lens implantation. Additionally, the administration of diflunisal after the surgically induced impairment of vision of the eye can improve or restore visual acuity loss to acceptable levels, particularly in patients who have developed cystoid macular edema after cataract removal surgery and/or subsequent artificial lens implantation.

A pharmaceutical composition in topical dosage unit form comprising diflunisal, a pharmaceutically acceptable dispersion medium, optionally a wetting agent, and optionally a pharmaceutically acceptable structured vehicle is provided as well.

BACKGROUND OF THE INVENTION

A complication of seemingly successful ophthalmic surgical procedures is a gradual or a sudden impairment of vision. This complication is commonly reported in patients after cataract removal, although it has been observed after surgical procedures such as scleral buckles, and is generally believed to be due to vascular incompetence, vitrous traction and inflammation of the vascular region of the eye. The same type of vision impairment has been observed in patients who have undergone a subsequent artificial lens implantation as well; however, incidence appears to be slightly lower in the pseudophakic patients when compared with aphakic patients. S. Severin, *American Journal of Ophthalmology*, 90:223–225, 1980.

Approximately five percent of cataract patients demonstrate these symptoms. The onset of this disease, commonly termed cystoid macular edema, most frequently occurs from four to sixteen weeks after cataract extraction. However, vision loss has been reported to manifest itself as long as thirteen years after cataract extraction. The diagnosis of cystoid macular edema is most frequently confirmed with a fluorescein angiogram which detects leaking of fluorescein from the optic disk and the macular capillaries as well as other retinal capillaries.

Approximately 70 percent of the patients suffering these complications after surgery recover spontaneously but recovery may take up to one year. The remaining group continues to suffer chronic vision loss.

There have been various attempts to resolve or to prevent this vision loss including topical administration of indomethacin, topical administration of corticosteroids, topical administration of combinations of indomethacin and corticosteroids, oral administration of indomethancin, oral administration of corticosteriods, implantation of an ultraviolet chromophore, and injection of betamethasone.

Indomethacin treatment has met with mixed results, however.

Yannuzzi et al, *Ophthalmology*, 88:9:947–953, 1983, conducted a study using a pretreatment of topical administration of 1 percent aqueous indomethacin to reduce the incidence of aphakic cystoid macular edema (ACME) after acknowledging that oral administration of indomethacin had been ineffective, in part due to the high incidence of gastrointestinal and central nervous system side effects. Their study indicated that the short term effects of topical indomethacin pretreatment were positive, reducing the incidence of ACME, but that by 12 to 18 months after surgery, the effect was insignificant. Furthermore, Yannuzzi et al concluded that there was no evidence that the most critical aspect to visual rehabilitation of the macula, central vision, benefited from prophylactic indomethacin pretreatment.

Miyake et al studied the topical administration of indomethacin in the prevention of cystoid macular edema after retinal detachment surgery. Their study found some early postoperative efficacy of the treatment but could not establish long term effects, i.e., greater than twelve weeks after surgery. K. Miyake, et al *American Journal of Ophthalmology*, 95:451–456, 1983.

Jampol has reported other unsuccessful attempts at topical indomethacin treatment. He also reported that combinations of topical indomethacin with topical corticosterioids had questionable short term results and a high rate of relapse. L. Jampol, *Ophthalmology*, 92:6:807–810, June, 1985.

The results of oral indomethacin administration studies have been equally as inconclusive. Postoperative, but presymptomatic treatment with indomethacin has resulted in a short term lower incidence, but not in an elimination of aphakic cystoid macular edema. However, long term effects could not be determined because of poor patient compliance due to the undesirable side effects of the medication including gastrointestinal irritation and neurological symptoms. R. Klein, et al. *American Journal of Ophthalmology* 87:487–489, 1979.

Jampol has also suggested the use of indomethacin and other non-steroids for the prophylaxis of aphakic cystoid macular edema and the use of corticosteroids for temporary beneficial therapeutic effects with respect to cystoid macular edema. However, the side effects of both indomethacin and corticosteroids make such treatment impractical. As an alternative treatment, Jampol has additionally suggested the placement of an ultraviolet radiation absorbing chromophore in a posterior chamber intraocular lens implant. L. Jampol, *Archives of Ophthalmology*, 103:1134–1135, August 1985.

Other experimental methods of treatment have comprised the injection of betamethasone directly into the subtendon space and the oral administration of indomethacin after the diagnosis of cystoid macular edema has been confirmed by fluorescein angiography. This did not result in success in a study conducted at the University of California, San Francisco, but topical corticosteroid treatment was suspected to have contributed to vision improvement. The resolution of vision could not be directly related to the topical corticosteroid treatment, however. S. Severin, *American Journal of Ophthalmology*, 90:223–225, 1980. See also, D. Jacobson et al, *American Journal of Ophthalmology*, 77:4:445–447, April 1974.

Witzel et al, U.S. Pat. No. 4,720,503, disclose the use of N-substituted fused-heterocyclic carboxamide derivatives to inhibit both cyclooxygenase and lipoxygenase production in the topical treatment of eye inflammation. However, Witzel et al explain that while cyclooxygenase inhibitors alone, such as diflunisal, inhibit only the process wherein arachidonic acid is oxygenated via cyclooxygenase to prostaglandins and thromboxanes, 5-lipoxygenase inhibitors are linked to the treatment of eye inflammation.

A treatment for the loss of vision induced by ophthalmic surgery and particularly induced by cystoid macular edema has been elusive for well over the last fifteen years.

Diflunisal is a prostaglandin synthetase inhibitor that has proven useful in the treatment of various inflammatory disease of the skelato-muscular system.

Ruyle et al, U.S. Pat. Nos. 3,681,445, 3,714,226, and 4,044,049, disclose oral administration of diflunisal in the treatment of inflammatory diseases, particularly rheumatoid arthritis, osteoarthritis, gout, infectious arthritis and rheumatic fever. However, diflusinal has been contradicted for treatment of the eye. Adverse eye findings have been reported with agents in the class of diflunisal, and peripheral edema has been observed in patients being treated with diflunisal. (*Physician's Desk Reference*, 43rd Edition, Medical Economics Company, Inc., 1989).

Sunshine et al, U.S. Pat. No. 4,749,721, disclose the use of diflunisal in combination with other active ingredient(s) for the relief of cough, cold and coldlike symptoms.

Dorn, U.S. Pat. No. 4,542,158, discloses the use of esters of diflunisal as anti-inflammatories with low irritancy of the mucous membranes particularly in the treatment of rheumatoid arthritis, osteoarthritis, gout, infectious arthritis, and rheumatic fever. Dorn also discloses that the esters can be contained in a cream, ointment, jelly, solution or suspension for topical application.

A novel method of use of diflunisal has now been discovered which results in the prevention or improvement of vision loss which typically occurs after ophthalmic surgery. In the present invention, diflunisal is administered to a subject either preoperatively, preoperatively and postoperatively but presymptomatically, postoperatively but presymptomatically, or postsymptomatically in correspondingly prophylactically effective amounts or therapeutically effective amounts sufficient to prevent the loss of visual acuity or to improve the visual acuity of the subject.

It is a further object of the invention to provide a topical dosage unit of diflunisal, particularly for use in the above method.

SUMMARY OF THE INVENTION

According to the present invention, there is provided a method for preventing impairment of vision of a warm-blooded animal induced by ophthalmic surgery comprising (i) administering a prophylactically effective amount of diflunisal to the animal. Preferably, the administration is either systemic or topical to the surface of the subject's eye(s).

The invention also contemplates a method for improving the vision of a warm-blooded animal which has been impaired by ophthalmic surgery comprising (i) administering a therapeutically effective amount of diflunisal to the animal. The administration, preferably, is either systemic or topical to the surface of the affected eye. In a further preferred embodiment, after administering the therapeutically effective amount (ii), a maintenance effective amount, which may be the same as or different than the therapeutically effective amount, of diflunisal may be administered in the same or different manner than the therapeutic administration.

The invention also provides a pharmaceutical composition in topical dosage unit form comprising a suspension of diflunisal, a pharmaceutically acceptable dispersion medium, optionally a wetting agent and optionally a structured vehicle to keep defloculated particles in a suspension, for example, aqueous solutions of polymeric materials, such as hydrocolloids, which are usually negatively charged in aqueous solutions.

The method of administration of diflunisal as described above can prevent, ameliorate, resolve or reverse loss or reduction of visual acuity in an eye caused by ophthalmic surgery, particularly, cataract removal surgery and/or subsequent artificial lens implantation, and most particularly, wherein the surgery has induced cystoid macular edema.

DETAILED DESCRIPTION OF THE INVENTION

A novel method for preventing impairment of vision of a warm-blooded animal caused by ophthalmic surgery comprising (i) administering a prophylactically effective amount of diflunisal to the animal is provided.

A novel method is also provided of improving the vision of a warm-blooded animal impaired by ophthalmic surgery comprising (i) administering a therapeutically effective amount of diflunisal to the animal. The improvement of the impairment of the vision or visual acuity can be a complete resolution, a reduction, a reversal or any amelioration of the vision of the eye.

The medicament utilized in the method of the present invention comprises diflunisal. Diflunisal is 2',4'-difluoro-4-hydroxy-3-biphenylcarboxylic acid, having an empirical formula of $C_{13}H_8F_2O_3$ and a structural formula of

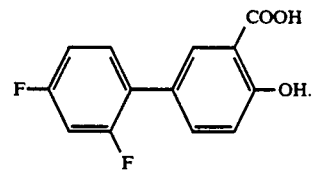

(PDR, 43rd Edition)

Diflunisal has a molecular weight of 250.2 and is a stable white, crystalline compound with a melting of 211–213° C. It is practically insoluble in water at neutral or acidic pH, but dissolves readily in dilute alkali and is soluble in most organic solvents including ethanol, methanol, and acetone.

Diflunisal is a prostaglandin synthetase inhibitor. It is a non-steroidal drug with analgesic, anti-inflammatory and antipyretic properties; however, its precise mechanism of analgesic and anti-inflammatory actions is not known.

It is commercially available as DOLOBID ® (Merck, Sharp and Dohme - West Point - PA) in 250 mg and 500 mg capsule-shaped, film-coated tablets and is recommended for the treatment of mild to moderate pain, osteoarthritis, and rheumatoid arthritis.

It has been found to have a lower incidence of side effects typical to analgesics such as dizziness, gastrointestinal adverse experiences, edema and tinnitus.

Preferably, in the present invention, diflunisal is administered to the patient either systemically or topically. Systemic administration can be oral, parenteral, intravenous, or through the skin absorption. Most preferably, systemmic administration is oral. Topical administration is preferably by drops of a suspension of diflunisal directly onto the surface of the eye.

Many types of ophthalmic surgery can induce vision loss and, particularly, induce cystoid macular edema.

The present invention is most effective with visions impairment due to ophthalmic surgical procedures such as cataract removal surgery including anterior chamber and posterior chamber procedures, intracapsular and extracapsular extraction with or without posterior capsulotomy, and optionally subsequent or simultaneous artificial lens implantation.

Cystoid macular edema is diagnosed by various procedures but is most commonly diagnosed by fluorescein angiography. It is believed to be caused by increased intraretinal capillary permeability of the macular region of the eye. While not intending to be bound by any theory, it is possible that an inhibition of any increased intracapillary permeability of the macular region of the eye or a reduction of the increased intracapillary permeability of the macular region of the eye should inhibit cystoid macular edema. Correspondingly, visual acuity should improve or should not become impaired.

Prophylactically effective amounts of diflunisal will depend upon the age, weight, sex, sensitivity, and the like of the individual patient. Preferably, prophylactically effective amounts of diflunisal will be intracapillary permeability increase inhibiting amounts of diflunisal sufficient to prevent vision loss. Typically, the amount will range from about 250 mg to about 1000 mg per day or every other day commencing either before or after the ophthalmic surgery but before any impairment is diagnosed with traditional methods of diagnosis including fluorescein angiography in the case of cystoid macular edema. Therefore, the prophylactically effective amount can include preoperative and/or postoperative periods of administration.

Preferably, the daily dosage will be divided into more than one administration unit per day, and most preferably, it will be administered as about 250 mg daily, about 500 mg every other day, about 500 mg daily or about 500 mg twice daily. If the administering of the prophylactically effective amount is to begin postoperatively, it is preferable to begin it from about the first postoperative day to about the seventh postoperative day. The daily amount can be varied or adjusted from time to time to comprise the prophylactically effective amount.

The prophylactically effective amount terminates when the threat of the development of the impairment to the vision is no longer significant, which preferably is up to about seven days after the surgery but may continue longer.

Therapeutically effective amounts of deflunisal will also depend upon the age, weight, sex, sensitivity and the like of the individual patient. Preferably, therapeutically effective amounts of diflunisal will be intracapillary permeability reducing amounts of deflunisal sufficient to improve the vision. Typically, the amount will range from about 250 mg to about 1000 mg per day from the onset or the diagnosis of the vision loss or as soon thereafter as practical and administration will terminate when the patient's vision has returned to its pre-impaired acuity or when no further improvement can be expected.

Preferably, the dosage will be divided into more than one administration unit per day, and most preferably, it will be administered as from about 250 mg twice daily to about 500 mg twice daily. This daily amount can be varied or adjusted from time to time to comprise the total therapeutically effective amount.

Patients may also require a maintenance effective amount of diflunisal after either the prophylactically effective amount or the therapeutically effective amount to assure that an impairment will not develop or to assure that the improvement in visual acuity remains and that there is little or no retrogression from post treatment vision. The maintenance effective amount should be administered either immediately after the therapeutically effective amount has been administered or as soon thereafter as practical.

Maintenance effective amounts of diflunisal will depend upon the age, weight, sex, sensitivity and the like of the individual patient as well. Preferably, maintenance effective amounts of diflunisal will be those amounts which will inhibit any further increases in intracapillary permeability after intracapillary permeability has been either initially inhibited or reduced. Typically, the amount will range from about 250 mg to about 500 mg every day or every other day. Preferably, the dosage may be divided into more than one administration unit per day or every other day. Most preferably, it will be administered as about 250 mg daily, about 500 mg daily or about 500 mg every other day. The daily amount can be varied or adjusted from time to time to comprise the maintenance effective amount.

The maintenance effective amount is terminated when the possibility of any recurrence of loss of visual acuity from the level of acuity obtained by administering the prophylactically effective or the therapeutically effective amount is insignificant. Preferably, the administering of the maintenance effective amount will be completed within about six months, but it may continue for the entire lifespan of the patient.

If a new or further impairment of the visual acuity of the subject who has been administered the prophylectically effective amount or the therapeutically effective amount is noted, it may be necessary to begin a new administration of a therapeutically effective amount of diflunisal. A maintenance effective amount of diflunisal may be prescribed thereafter as well.

The pharmaceutically acceptable dispersion medium, pharmaceutically acceptable wetting agents and pharmaceutically acceptable structured vehicles, of the present invention are those compatible with diflunisal and are known to one of ordinary skill in the pharmaceutical arts and described in Remington's Pharmaceutical Science, 17th Edition, Mack Publishing Company, 1985. The suspension may be made in any manner commonly known to those of ordinary skill in the pharmaceutical arts as well.

DESCRIPTION OF THE PREFERRED EMBODIMENTS

The following examples illustrate the invention without limitation.

EXAMPLE 1

A posterior chamber implant with cataract removal procedure was performed on the right eye of a 77 year old woman. Two months after the procedure, a diagnosis of cystoid macular edema was confirmed by fluorescein angiography, and visual acuity of the right eye was measured at 20/200. The patient was placed on a regimen of 500 mg of DOLOBID ® (diflunisal—Merck, Sharp & Dohme) twice daily. Five months later, visual acuity of the right eye had improved to 20/40.

EXAMPLE 2

An anterior chamber implant with cataract removal procedure was performed on the right eye of a 74 year old woman. Fourteen months after the procedure, a diagnosis of cystoid macular edema was confirmed by fluorescein angiography, and visual acuity of the right eye was measured at 20/200. The patient was placed on a regimen of 500 mg of DOLOBID ® (diflunisal—Merck, Sharp & Dohme) twice daily. Six months later, visual acuity of the right eye had improved to 20/70.

EXAMPLE 3

A cataract removal procedure was performed on the right eye of a 59 year old man. Three years later, a secondary artificial lens implant was performed on the same eye. One year after the second procedure, a diagnosis of cystoid macular edema was made, and visual acuity of the right eye was measured at 20/200. The patient was placed on a regimen of 500 mg of DOLOBID ® (diflunisal—Merck, Sharp & Dohme) twice daily. Two and one half months later, visual acuity of the right eye had improved to 20/80.

EXAMPLE 4

An anterior chamber implant with cataract removal procedure was performed on the left eye of an 80 year old woman. Thirteen months after the procedure, a YAG laser procedure was performed on the left eye, and visual acuity of the left eye was measured at 20/80. Two months after the second procedure, a diagnosis of cystoid macular edema was confirmed by fluorescein antiography, and visual acuity of the left eye was measured at 20/200. The patient was placed on a regimen 500 mg of DOLOBID ® (diflunisal—Merck, Sharp & Dohme). Eight months later, visual acuity of the left eye had improved to 20/40.

EXAMPLE 5

A posterior chamber implant with cataract removal procedure was performed on the left eye of a 77 year old man. Eighteen months after the procedure, a diagnosis of cystoid macular edema was confirmed by fluorescein angiography, and visual acuity of the left eye was measured at CF 6' (count fingers at six feet). The patient was placed on a regimen of 500 mg DOLOBID ® (diflunisal—Merck, Sharp & Dohme) 8 months later visual acuity of the left eye had improved to 20/70.

EXAMPLE 6

A retinal detachment in the left eye of a 64 year old woman was surgically repaired with a buckle procedure. Visual acuity after the buckle procedure resolved to 20/80. Approximately 3½ years later, cystoid macular edema was diagnosed by fluorescein angiography in the left eye. Four and one half months later, the patent was placed on a regimen of 500 mg of DOLOBID ® (diflunisal—Merck, Sharp & Dohme) twice daily. After two months of treatment, the visual acuity in the eye was measured as 20/40. The subject discontinued the medication, and four months later, visual acuity of the left eye was measured at 20/80.

EXAMPLE 7

An anterior chamber implant with cataract removal procedure was performed on the right eye of a 66 year old woman. Seven years later, a secondary artificial lens implantation procedure was performed on the same eye. Two years subsequent to the lens implantation, a diagnosis of cystoid macular edema was confirmed by fluorescein angiography, and visual acuity of the right eye was measured at 20/200. The patient was placed on a regimen of 500 mg of DOLOBID ® (diflunisal—Merck, Sharp & Dohme) twice daily. Twenty-one months later, visual acuity of the right eye had improved to 20/40. The medication was discontinued. Two months later, visual acuity of the right eye was measured at 20/50, and the patient was again placed on a regimen of 500 mg of DOLOBID ® twice daily. Six months later, visual acuity of the right eye had improved to 20/40.

EXAMPLE 8

A posterior chamber implant with cataract removal procedure was performed on the right eye of a man. Four months later, a diagnosis of cystoid macular edema was confirmed by fluorescein angiogram, and visual acuity of the right eye was measured at 20/60. The patient was placed on a regimen of 500 mg of DOLOBID ® (diflunisal—Merck, Sharp & Dohme) twice daily. Nine months later, visual acuity of the right eye had improved to 20/30, and the medication was discontinued. Eleven months later, visual acuity of the right was measured at 20/200, and the patient was again placed on a regimen of 500 mg of DOLOBID ® twice daily. Seven months later, visual acuity of the right had improved to 20/40.

EXAMPLE 9

A posterior chamber implant with cataract removal procedure was performed on the right eye of a man. Three months later, a diagnosis of cystoid macular edema was confirmed by fluorescein angiography, and visual acuity of the right eye was measured at 20/200. The patient was placed on a regimen of 500 mg of DOLOBIT ® (diflunisal—Merck, Sharp & Dohme) twice daily. Ten months later, visual acuity of the right eye had improved to 20/50.

EXAMPLE 10

An anterior chamber implant with cataract removal procedure was performed on the right eye of a 63 year old man. Six years later, a diagnosis of cystoid macular edema was confirmed by fluorescein angiography, and visual acuity of the right eye was measured at 20/50. The patient was placed on a regimen of 500 mg of DOLOBID ® (diflunisal—Merck, Sharp & Dohme) twice daily. Ten months later, visual acuity of the right eye had improved to 20/25.

EXAMPLE 11

An anterior chamber implant with cataract removal procedure was performed on the left eye of a 68 year old woman. Three months later, a diagnosis of cystoid macular edema was confirmed by fluorescein angiography, and visual acuity of the left eye was measured at 20/200. The patient was placed on a regimen of 500 mg of DOLOBID ® (diflunisal—Merck, Sharp & Dohme)

twice daily. Six months later, visual acuity of the left eye had improved to 20/20.

EXAMPLE 12

An anterior chamber implant with cataract removal procedure was performed on the left eye of an 80 year old woman. Four months later, a diagnosis of cystoid macular edema was confirmed by fluorescein angiography, and visual acuity of the left eye was measured at 20/300. The patient was placed on a regimen of 500 mg of DOLOBID ® (diflunisal—Merck, Sharp & Dohme) twice daily. Three months later, visual acuity of the left eye had improved to 20/50.

EXAMPLE 13

An anterior chamber implant with cataract removal procedure was performed on the right eye of an 80 year old woman. Six months later, a diagnosis of cystoid macular edema was confirmed by fluorescein angiography, and visual acuity of the right eye was measured at 20/400. The patient was placed on a regimen of 500 mg of DOLOBID ® (diflunisal—Merck, Sharp & Dohme) twice daily. Three months later, visual acuity of the right eye had improved to 20/30.

EXAMPLE 14

A posterior chamber implant with cataract removal procedure was performed on the right eye of a 77 year old man. Four months later, a diagnosis of cystoid macular edema was confirmed by fluorescein angiography, and visual acuity of the right eye was measured at 20/200. The patient was placed on a regimen of 500 mg of DOLOBID ® (diflunisal—Merck, Sharp & Dohme) twice daily. One month later, visual acuity of the right eye had improved to 20/100. However, two months later, the patient developed severe gastrointestinal bleeding, and the medication was stopped.

COMPARATIVE EXAMPLE 15

A 64 year old man suffered a retinal detachment of the left eye due to non-surgical trauma. Visual acuity of the left eye was measured at 20/30. Eleven days later, a scleral buckle procedure was performed. Five months later, a diagnosis of cystoid macular edema was confirmed by fluorescein angiography, and visual acuity of the left eye was measured at 20/60. The patient was placed on a regimen of 500 mg of DOLOBID ® (diflunisal—Merck, Sharp &Dohme) twice daily. Fifteen months later, visual acuity of the left eye still measured 20/60.

COMPARATIVE EXAMPLE 16

A 56 year old man suffered a non-surgical trauma to the left eye. Two years later a cataract in the left eye was diagnosed. Visual acuity of the left eye was measured at 20/200, and an anterior chamber implant with cataract removal procedure was performed. Visual acuity improved to 20/40 following the procedure. Six months later, a diagnosis of cystoid macular edema was confirmed by fluorescein angiography, and visual acuity of the left eye was measured at 20/200. Three years after the diagnosis of cystoid macular edema, visual acuity of the left eye had decreased to "count fingers vision". The patient was placed on a regimen of 500 mg of DOLOBID ® (diflunisal—Merck, Sharp & Dohme) twice daily. Six months later, visual acuity of the left eye still remained as "count fingers vision".

COMPARATIVE EXAMPLE 17

An anterior chamber implant with cataract removal procedure was performed on the left eye of an 85 year old woman. Three weeks later, a diagnosis of herpes simplex virus infection and secondary cystoid macular edema was made, and visual acuity of the left eye was measured at 20/400. Seven weeks later, the diagnosis of cystoid macular edema was confirmed by fluorescein angiography, and the patient was placed on a regimen of 500 mg of DOLOBID ® (diflunisal—Merck, Sharp & Dohme) twice daily. Eight months later, visual acuity of the left eye remained at 20/400.

COMPARATIVE EXAMPLE 18

An anterior chamber implant with cataract removal procedure was performed on the right eye of an 82 year old woman. A post surgical trauma caused vitreous fluid loss. One year later, a diagnosis of cystoid macular edema was confirmed by fluorescein angiography, and visual acuity of the right eye was measured at 20/60. The patient was placed on a regimen of 500 mg of DOLOBID ® (diflunisal—Merck, Sharp & Dohme) twice daily. Three months later, visual acuity of the left eye remained at 20/60.

Examples 1-14 indicate that treatment with diflunisal after surgical procedures including cataract extraction, intraocular lens implantation, retinal surgery, and YAG laser treatment is effective in ameliorating vision impairment due to ophthalmic surgery, and/or due to cystoid macular edema occurring secondarily to those procedures.

Comparative Examples 15-18 indicate that non-surgically induced vision loss or surgically induced vision loss accompanied by secondary complications does not respond well to diflunisal treatment.

All patents, publications, applications and test methods mentioned above are hereby incorporated by reference.

Many variations of the present invention will suggest themselves to those skilled in the art in light of the above, detailed description. For example, the amounts of diflunisal may be adjusted downward for pediatric use. All such obvious variations are within the full intended scope of the appended claims.

I claim:

1. A method of improving the vision of a warm-blooded animal impaired by cystoid macular edema comprising systemically administering a therapeutically effective amount of diflunisal to said warm-blooded animal.

2. A method as defined in claim 1 wherein said therapeutically effective amount comprises up to about 1000 mg daily.

3. A method as defined in claim 2 wherein said therapeutically effect amount of diflunisal is administered in more than one administration unit daily.

4. A method as defined in claim 1 comprising beginning administration of diflunisal when said cystoid macular edema is diagnosed.

5. A method as defined in claim 2, wherein the effective amount is about 500 mg/every other day.

6. A method as defined in claim 2, wherein said effective amount is about 500 mg daily.

7. A method as defined in claim 2 wherein said effective amount is 250 mg/daily,.

8. A method for treating cystic macular edema in the eye of a warm-blooded animal comprising (i) orally administering to a said animal from 500 to 1000 mg daily of diflunisal; and (ii) subsequently orally administering a maintenance effective amount of from about 250 to about 500 mg daily every other day of diflunisal.

9. A method of improving the vision of a warm-blooded animal impaired by cystoid macular edema induced by ophthalmic surgery comprising (i) administering a therapeutically effective amount of diflunisal to said warm-blooded animal after the cystoid macular edema has been diagnosed.

10. A method as defined in claim 9 wherein said ophthalmic surgery is cataract removal surgery.

11. A method as defined in claim 10 wherein said cataract removal surgery is performed simultaneously with or is followed by artificial lens implant surgery.

* * * * *